US012721932B2

(12) United States Patent
Lu et al.

(10) Patent No.: US 12,721,932 B2
(45) Date of Patent: Sep. 1, 2026

(54) HYDROPHILIC SILICONE RUBBER SERVING AS MEDICAL CATHETER, PREPARATION METHOD THEREOF AND APPLICATION THEREOF

(71) Applicant: SHANDONG UNIVERSITY, Jinan (CN)

(72) Inventors: Haifeng Lu, Jinan (CN); Chuanjian Zhou, Jinan (CN); Shengyu Feng, Jinan (CN); Hua Wang, Jinan (CN); Chen An, Jinan (CN); Yuan Qu, Jinan (CN); Fanzhen Kong, Jinan (CN); Qingming Zeng, Jinan (CN)

(73) Assignee: SHANDONG UNIVERSITY, Jinan (CN)

( * ) Notice: Subject to any disclaimer, the term of this patent is extended or adjusted under 35 U.S.C. 154(b) by 668 days.

(21) Appl. No.: 18/266,279

(22) PCT Filed: Jul. 28, 2021

(86) PCT No.: PCT/CN2021/108793

§ 371 (c)(1),
(2) Date: Jun. 9, 2023

(87) PCT Pub. No.: WO2022/121328

PCT Pub. Date: Jun. 16, 2022

(65) Prior Publication Data

US 2024/0042105 A1 Feb. 8, 2024

(30) Foreign Application Priority Data

Dec. 9, 2020 (CN) ......................... 202011424822.4

(51) Int. Cl.

| | |
|---|---|
| ***C08F 2/46*** | (2006.01) |
| ***A61L 29/06*** | (2006.01) |
| ***C08F 2/50*** | (2006.01) |
| ***C08G 61/04*** | (2006.01) |
| ***C08K 3/04*** | (2006.01) |
| ***C08K 5/37*** | (2006.01) |

(52) U.S. Cl.
CPC ................ *A61L 29/06* (2013.01); *C08K 3/04* (2013.01); *C08K 5/37* (2013.01)

(58) Field of Classification Search
CPC .............. C08K 5/37; C08K 3/04; A61L 29/06
USPC ................. 522/44, 6, 1, 71, 189, 184; 520/1
See application file for complete search history.

(56) References Cited

U.S. PATENT DOCUMENTS 5,432,226 A 7/1995 Aonuma et al.

FOREIGN PATENT DOCUMENTS

| | | | |
|---|---|---|---|
| CN | 105315469 A | 2/2016 | |
| CN | 105601928 A | 5/2016 | |
| CN | 105778105 A | 7/2016 | |
| CN | 106046379 A | * 10/2016 | ............ C08G 77/20 |
| CN | 106496566 A | 3/2017 | |
| CN | 112538271 A | 3/2021 | |

OTHER PUBLICATIONS

Zhang et al, CN 106046379 Machine Translation, Oct. 26, 2016 (Year: 2016).*
International Search Report of PCT Patent Application No. PCT/CN2021/108793 issued on Sep. 15, 2021.
Yue Zhang, Functionalization and Material Preparation of Aminopropyl—Containing Siloxane, Thesis for Master Degree, 2017.
1st Office Action of Chinese Patent Application No. 202011424822.4 issued on Jul. 12, 2021.
2nd Office Action of Chinese Patent Application No. 202011424822.4 issued on Nov. 15, 2021.

* cited by examiner

*Primary Examiner* — Jessica Whiteley

(57) ABSTRACT

The present disclosure relates to hydrophilic silicone rubber serving as a medical catheter and a preparation method and application thereof. The hydrophilic silicone rubber is obtained from polysiloxane containing a nitrile group through a formula design and ultraviolet light irradiation, and can be applied to preparation of silicon rubber medical catheters. The hydrophilic silicone rubber prepared in the present disclosure is cross-linked by ultraviolet irradiation, without a transition metal catalyst, and without metal ion residues. The hydrophilic silicone rubber prepared in the present disclosure can be directly taken as a medical catheter for use, or as a basic formula for use after adding other auxiliary ingredients, so as to meet special needs of various medical places.

14 Claims, 1 Drawing Sheet

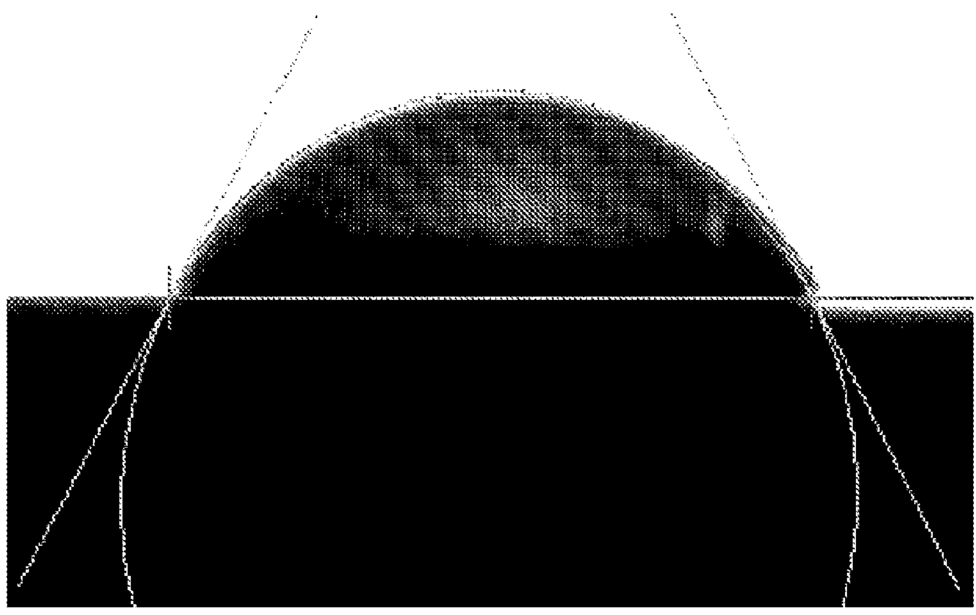

HYDROPHILIC SILICONE RUBBER SERVING AS MEDICAL CATHETER, PREPARATION METHOD THEREOF AND APPLICATION THEREOF

FIELD

The present disclosure relates to hydrophilic silicone rubber serving as a medical catheter, and belongs to the field of polymer material preparation and application.

BACKGROUND

Silicone rubber is an elastomer material with a silicon-oxide-silicon bond as a main chain, which differs from an ordinary elastomer with a carbon-carbon bond as a main chain and has unique properties. The silicone rubber may be used for a long time at a room temperature, for example, a service life at 120° C. is 10 years. Because of excellent high-temperature resistance, anti-aging performance, anti-coagulant performance, biocompatibility and chemical inertia, a silicone rubber product may be implanted in a human body for a long time. In theory, it is not necessary to regularly take out and replace the silicone rubber product. A preparation process of the silicone rubber does not require the addition of a plasticizer, thus avoiding the problem of plasticizer seepage during use. This characteristic determines the advantageous position of the silicone rubber in the medical industry, especially in the field of human implantation.

The silicone rubber, as an important medical material, has achieved good performance in years of clinical trials and has been widely recognized by the medical community, and there are hundreds of varieties and tens of thousands of series of its products. Since the 1960s, many applications of the silicone rubber as human implant materials and medical products have emerged both domestically and internationally. Typical products include the following types:

(1) products for ophthalmology and otorhinolaryngology, including artificial nose bridges, artificial chins, nostril stents and other artificial organs;

(2) products for a digestive system, such as gastric tubes, gastric decompression tubes, gastric volume reduction balls and other medical instruments;

(3) products for a craniocerebral department, such as artificial skulls and external ventricular drainage tubes;

(4) products for a cardiac surgery department, such as thoracic drainage tubes, thoracic isolation membranes and other instruments;

(5) products for an abdominal surgery, such as single lumen catheters; and (6) products for a reproductive system and other products.

In addition to the above application as the medical products, the silicone rubber may further be taken as a carrier for a drug delivery system, such as encapsulated capsules for antibiotics, sedatives, sleeping pills, anticancer drugs and other drugs, which is taken orally; or may be made into a subcutaneous implant and used through subcutaneous injection; or may be made into skin adsorbing formulations for use through transdermal absorption.

Gastrointestinal medical treatment is a major application field of silicone rubber medical catheters, and typical products include: gastric tubes, gastric volume reduction balls, gastric bands, intestinal obstruction catheters, duodenal tubes, double lumen cannulas, gastric fistulas, and Sengstaken-Blakemore hemostatic catheters. However, a surface of the silicone rubber has high hydrophobicity, which makes the silicone rubber have poor adhesion to tissue and cells and great friction, bringing great discomfort and pain to patients. By surface modification or bulk modification, the hydrophilicity of medical silicone rubber materials can be improved. Typical modification methods include surface grafting, plasma treatment and other methods. However, surface-modified hydrophilic coatings have the disadvantages of being prone to detachment and short in service life. Further research is currently needed.

SUMMARY

As for a current situation that there is no long-term hydrophilic silicone rubber medical catheter in the prior art, the present disclosure provides hydrophilic silicone rubber capable of being used as a medical catheter and a preparation method and application thereof. In the present disclosure, the hydrophilic silicone rubber is prepared based on modified polysiloxane, and may be applied in the field of silicone rubber medical catheters. The hydrophilic silicone rubber prepared in the present disclosure is cross-linked by ultraviolet irradiation, without use of a transition metal catalyst, and without residual metal ions. The hydrophilic silicone rubber prepared in the present disclosure can be directly taken as a medical catheter for use, or as a basic formula for use after adding other auxiliary ingredients, so as to meet special needs of various medical places.

Overview

The present disclosure provides hydrophilic silicone rubber prepared based on modified polysiloxane, which is obtained from polysiloxane containing a nitrile group through formula design and ultraviolet light irradiation, and may be applied in the field of silicon rubber medical catheters. The hydrophilic silicone rubber prepared in the present disclosure is cross-linked by ultraviolet irradiation, without use of a transition metal catalyst, and without residual metal ions. The hydrophilic silicone rubber prepared in the present disclosure can be directly taken as a medical catheter for use, or as a basic formula for use after adding other auxiliary ingredients, so as to meet special needs of various medical places.

DETAILED DESCRIPTION

The technical solution of the present disclosure is as follows:

a preparation method of hydrophilic silicone rubber includes the following steps:

mixing methyl vinyl silicone raw rubber containing a nitrile group with a reinforcing agent, a multi-sulfhydryl compound and a catalyst, and performing ultraviolet light irradiation crosslinking curing to obtain the hydrophilic silicone rubber.

According to the present disclosure, preferably, the methyl vinyl silicone raw rubber containing the nitrile group is methyl vinyl silicone raw rubber containing the nitrile group on a side chain, further preferably, methyl vinyl silicone raw rubber with a molecular weight of 20000-40000 and containing the nitrile group on the side chain.

According to the present disclosure, preferably, the reinforcing agent is white carbon black, further preferably, the reinforcing agent is precipitated white carbon black.

According to the present disclosure, preferably, the multi-sulfhydryl compound is a compound containing at least two sulfhydryl groups in a molecule, further preferably, the multi-sulfhydryl compound is tetra (3-mercaptopropionic acid) pentaerythritol ester.

According to the present disclosure, preferably, the catalyst is 2,2-dimethoxy-2-phenylacetophenone (DMPA).

According to the present disclosure, preferably, a weight ratio of the methyl vinyl silicone raw rubber containing the nitrile group to the reinforcing agent to the multi-sulfhydryl compound to the catalyst is 1000:(300-400):(30-50):(1-2).

According to the present disclosure, preferably, after the methyl vinyl silicone raw rubber containing the nitrile group is uniformly mixed with the reinforcing agent, the multi-sulfhydryl compound and the catalyst, bubbles are further removed by vacuumizing, and then ultraviolet light irradiation crosslinking curing is performed.

According to the present disclosure, preferably, time of the ultraviolet light irradiation crosslinking curing is 5-10 minutes.

According to the present disclosure, hydrophilic silicone rubber prepared by the above method is further provided.

According to the present disclosure, application of the above hydrophilic silicone rubber in human implant materials and medical products is further preferably for preparation of medical catheters.

According to the present disclosure, a use method of the above hydrophilic silicone rubber includes the following steps:

the hydrophilic silicone rubber is directly prepared as a medical catheter for use; or, as a basic formula for use after adding other auxiliary ingredients, so as to meet special needs of various medical places.

What is not described in detail in the present disclosure is based on the prior art.

The principle and the beneficial effects of the present disclosure are as follows:

in the present disclosure, the methyl vinyl silicone raw rubber containing the nitrile group on the side chain is selected, due to existence of the nitrile group, the hydrophilicity of a surface of the silicone rubber is changed, so that a silicone rubber material with good hydrophilicity is obtained. Since the nitrile group is chemically bonded on the side chain of the silicone rubber, it is different from a current popular scheme of modifying the silicone rubber, and a hydrophilic effect is lasting. The molecular weight of the methyl vinyl silicone raw rubber selected in the present disclosure is 20000-40000, and the methyl vinyl silicone raw rubber has good flowability and is conducive to the preparation of medical catheters with various complex shapes. In the present disclosure, the DMPA is used as the catalyst, which is different from an organic tin catalyst used by silicone rubber usually vulcanized at a room temperature, it does not contain heavy metals, and the physiological safety is high. In the present disclosure, a process of ultraviolet light curing is adopted, which can avoid damage to connected components of the catheters during conventional high-temperature crosslinking, and also avoid the long-time-consuming disadvantage of a conventional room-temperature shrinkage process. The hydrophilicity of the silicone rubber prepared in the present disclosure is far superior to that of ordinary silicone rubber, and significant effects are achieved. Therefore, it has a significant technological superiority.

The hydrophilic silicone rubber prepared in the present disclosure may be directly taken as the medical catheter for use, or as the basic formula for use after adding other auxiliary ingredients, the special needs of various medical places can be met, application prospects are broad, and market prospects are good.

BRIEF DESCRIPTION OF THE DRAWINGS

FIG. 1 is a picture of a water contact angle of hydrophilic silicone rubber obtained from Embodiment 2.

DETAILED DESCRIPTION OF THE EMBODIMENTS

The present disclosure is further described below through specific embodiments, but not limited to these.

Raw materials used in the embodiments are all conventional commercially available or synthesized according to reference methods.

The proportion of parts described in the embodiments is the proportion of mass.

Embodiment 1

Weighed 300 parts of precipitated white carbon black are added into 1000 parts of polysiloxane (with an average molecular weight of 23000) containing a nitrile group, and they are uniformly mixed with stirring. 50 parts of tetra (3-mercaptopropionic acid) pentaerythritol ester are added to therein and stirred for 5 minutes; 1 part of DMPA is added and stirred for 5 minutes, and the mixture is poured into a mold for leveling after the materials are uniformly mixed; after leveling, the mold is put into a dryer to remove bubbles by vacuumizing, and vacuumizing and deflation are performed 3 times; and finally, it is irradiated by ultraviolet light for 10 minutes for curing and crosslinking.

Embodiment 2

Weighed 300 parts of precipitated white carbon black are added into 1000 parts of polysiloxane (with an average molecular weight of 32000) containing a nitrile group, and they are uniformly mixed with stirring. 30 parts of tetra (3-mercaptopropionic acid) pentaerythritol ester are added therein and stirred for 5 minutes; then 1.2 parts of DMPA are added and stirred for 5 minutes, and the mixture is poured into a mold for leveling after the materials are uniformly mixed; after leveling, the mold is put into a dryer to remove bubbles by vacuumizing, and vacuumizing and deflation are performed 3 times; and finally, it is irradiated by ultraviolet light for 10 minutes for curing and crosslinking.

A water contact angle of the hydrophilic silicone rubber prepared in the embodiment is shown in FIG. 1, a left water contact angle is 58.8°, and a right water contact angle is 54.5°. It may be seen from FIG. 1 that the silicone rubber prepared in the present disclosure has good hydrophilicity. When used as a medical catheter, it can improve the adhesion between the silicone rubber and tissue and cells, reduce the friction caused by relative movement, and avoid discomfort and pain caused by hydrophobic silicone rubber to patients.

Embodiment 3

Weighed 300 parts of precipitated white carbon black are added into 1000 parts of polysiloxane (with an average molecular weight of 42000) containing a nitrile group, and they are uniformly mixed with stirring. 50 parts of tetra (3-mercaptopropionic acid) pentaerythritol ester are added therein and stirred for 5 minutes; then 1.5 parts of DMPA are added and stirred for 5 minutes, and the mixture is poured into a mold for leveling after the materials are uniformly mixed; after leveling, the mold is put into a dryer to remove bubbles by vacuumizing, and vacuumizing and deflation are performed 3 times; and finally, it is irradiated by ultraviolet light for 10 minutes for curing and crosslinking.

Experimental Example 1

The mechanical strength of the hydrophilic silicone rubber prepared in Embodiments 1, 2 and 3 is tested, and results are shown in Table 1.

TABLE 1

| Serial number of samples | Hardness (ShA) | Tensile strength (MPa) | Elongation at break (%) | Tear strength (KN/m) |
| --- | --- | --- | --- | --- |
| Embodiment 1 | 40 | 2.09 | 133 | 10.60 |
| Embodiment 2 | 42 | 2.31 | 150 | 10.51 |
| Embodiment 3 | 43 | 2.62 | 156 | 12.38 |

It may be seen from Table 1 that the silicone rubber prepared in the present disclosure has a good mechanical property, which ensures its ability to be used as a medical catheter.

What is claimed is:

1. A preparation method of hydrophilic silicone rubber, comprising the following steps:

mixing methyl vinyl silicone raw rubber containing a nitrile group with a reinforcing agent, a multi-sulfhydryl compound and a catalyst, and performing ultraviolet light irradiation crosslinking curing to obtain the hydrophilic silicone rubber.

2. The preparation method of the hydrophilic silicone rubber according to claim 1, wherein the methyl vinyl silicone raw rubber containing the nitrile group is methyl vinyl silicone raw rubber containing the nitrile group on a side chain.

3. The preparation method of the hydrophilic silicone rubber according to claim 2, wherein the methyl vinyl silicone raw rubber containing the nitrile group is methyl vinyl silicone raw rubber with a number-average molecular weight of 20000-40000 and containing the nitrile group on the side chain.

4. The preparation method of the hydrophilic silicone rubber according to claim 1, wherein the reinforcing agent is white carbon black;

preferably, the reinforcing agent is precipitated white carbon black.

5. The preparation method of the hydrophilic silicone rubber according to claim 4, wherein the multi-sulfhydryl compound is a compound containing at least two sulfhydryl groups in a molecule.

6. The preparation method of the hydrophilic silicone rubber according to claim 5, wherein the multi-sulfhydryl compound is tetra (3-mercaptopropionic acid) pentaerythritol ester.

7. The preparation method of the hydrophilic silicone rubber according to claim 1, wherein the catalyst is 2,2-dimethoxy-2-phenylacetophenone.

8. The preparation method of the hydrophilic silicone rubber according to claim 1, wherein a weight ratio of the methyl vinyl silicone raw rubber containing the nitrile group to the reinforcing agent to the multi-sulfhydryl compound to the catalyst is 1000:(300-400):(30-50):(1-2).

9. The preparation method of the hydrophilic silicone rubber according to claim 1, wherein after the methyl vinyl silicone raw rubber containing the nitrile group is uniformly mixed with the reinforcing agent, the poly-sulfhydryl compound and the catalyst, bubbles are further removed by vacuumizing, and then ultraviolet light irradiation crosslinking curing is performed.

10. The preparation method of the hydrophilic silicone rubber according to claim 1, wherein time of the ultraviolet light irradiation crosslinking curing is 5-10 minutes.

11. Hydrophilic silicone rubber obtained by the preparation method according to claim 1.

12. Application of the hydrophilic silicone rubber according to claim 11 in human implant materials and medical products.

13. The application according to claim 12, wherein the hydrophilic silicone rubber is used for preparing medical catheters.

14. A use method of the hydrophilic silicone rubber according to claim 11, comprising the following steps:

directly preparing the hydrophilic silicone rubber into a medical catheter for use; alternatively, as a basic formula, into a medical product for use after adding auxiliary ingredients.

* * * * *